United States Patent
Elahi et al.

(10) Patent No.: US 11,607,479 B2
(45) Date of Patent: Mar. 21, 2023

(54) OPTIMIZING PERITONEAL DIALYSIS USING A PATIENT HAND-HELD SCANNING DEVICE

(71) Applicants: BAXTER INTERNATIONAL INC., Deerfield, IL (US); BAXTER HEALTHCARE SA, Glattpark (CH)

(72) Inventors: Bijan Elahi, Lake Forest, IL (US); Ying-Cheng Lo, Green Oaks, IL (US); Vikram Prabhakar Mehendale, Waukegan, IL (US)

(73) Assignees: BAXTER INTERNATIONAL INC., Deerfield, IL (US); BAXTER HEALTHCARE SA, Glattpark (CH)

( * ) Notice: Subject to any disclaimer, the term of this patent is extended or adjusted under 35 U.S.C. 154(b) by 0 days.

(21) Appl. No.: 17/372,984

(22) Filed: Jul. 12, 2021

(65) Prior Publication Data
US 2021/0338913 A1 Nov. 4, 2021

Related U.S. Application Data

(63) Continuation of application No. 16/658,894, filed on Oct. 21, 2019, now Pat. No. 11,058,809, which is a
(Continued)

(51) Int. Cl.
*A61M 1/28* (2006.01)
*G16H 10/65* (2018.01)
(Continued)

(52) U.S. Cl.
CPC ............. *A61M 1/28* (2013.01); *G16H 10/60* (2018.01); *G16H 10/65* (2018.01); *G16H 20/17* (2018.01);
(Continued)

(58) Field of Classification Search
CPC ...................................................... A61M 1/28
See application file for complete search history.

(56) References Cited

U.S. PATENT DOCUMENTS

| | | | |
|---|---|---|---|
| 4,976,683 | A | 12/1990 | Gauthier et al. |
| 5,141,492 | A | 8/1992 | Dadson |

(Continued)

FOREIGN PATENT DOCUMENTS

| | | |
|---|---|---|
| EP | 1449548 | 8/2004 |
| EP | 1623731 | 2/2006 |

(Continued)

OTHER PUBLICATIONS

Japanese Office Action dated Jun. 3, 2014 for related Japanese Appln. No. 2012-534235.
(Continued)

*Primary Examiner* — Joseph D Burgess
(74) *Attorney, Agent, or Firm* — K&L Gates LLP (57) ABSTRACT

A handheld personal communication apparatus for dialysis includes a reader to read a marking displayed on a dialysis fluid container to acquire data concerning at least one of a dialysis fluid type or a dialysis fluid volume from the marking; a processor using the at least one of the dialysis fluid type or the dialysis fluid volume to determine a dialysis dwell time for at least one cycle of a dialysis therapy, the dialysis dwell time being a time to achieve, over the at least one cycle, at least one of (a) a specified ultrafiltrate level, (b) a urea removal level, or (c) a creatinine removal level; and an output interface providing an indication to the patient of a completion of the dialysis dwell time.

18 Claims, 6 Drawing Sheets

Related U.S. Application Data continuation of application No. 14/697,022, filed on Apr. 27, 2015, now Pat. No. 10,449,284, which is a continuation of application No. 12/826,183, filed on Jun. 29, 2010, now Pat. No. 9,020,827.

(60) Provisional application No. 61/252,363, filed on Oct. 16, 2009.

(51) Int. Cl.
  *G16H 20/40* (2018.01)
  *G16H 10/60* (2018.01)
  *G16H 20/17* (2018.01)

(52) U.S. Cl.
  CPC ..... *G16H 20/40* (2018.01); *A61M 2205/3553* (2013.01); *A61M 2205/3569* (2013.01); *A61M 2205/3592* (2013.01); *A61M 2205/52* (2013.01); *A61M 2205/6072* (2013.01)

(56) References Cited

U.S. PATENT DOCUMENTS

| | | | |
|---|---|---|---|
| 5,158,538 A | 10/1992 | Shaw | |
| 5,350,357 A | 9/1994 | Kamen et al. | |
| 5,372,147 A | 12/1994 | Lathrop, Jr. et al. | |
| 5,423,750 A | 5/1995 | Spiller | |
| 5,445,610 A | 8/1995 | Evert | |
| 5,555,897 A | 9/1996 | Lathrop, Jr. et al. | |
| 5,670,057 A | 9/1997 | Chen et al. | |
| 5,722,947 A | 3/1998 | Jeppsson et al. | |
| 5,827,820 A | 10/1998 | duMoulin et al. | |
| 5,843,474 A | 12/1998 | Williams | |
| 5,902,336 A | 5/1999 | Mishkin | |
| 5,938,634 A | 8/1999 | Packard | |
| 6,074,359 A | 6/2000 | Keshaviah et al. | |
| 6,117,122 A | 9/2000 | Din et al. | |
| 6,144,848 A | 11/2000 | Walsh et al. | |
| 6,232,286 B1 | 5/2001 | Goodearl et al. | |
| 6,234,992 B1 | 5/2001 | Haight et al. | |
| 6,495,366 B1 | 12/2002 | Briggs | |
| 6,497,676 B1 | 12/2002 | Childers et al. | |
| 6,558,667 B2 | 5/2003 | Nakanishi | |
| 6,585,677 B2 | 7/2003 | Cowan, Jr. et al. | |
| 6,592,542 B2 | 7/2003 | Childers et al. | |
| 6,595,948 B2 | 7/2003 | Suzuki et al. | |
| 6,685,831 B2 | 2/2004 | Donig et al. | |
| 6,814,547 B2 | 11/2004 | Childers et al. | |
| 6,932,787 B2 | 8/2005 | Cowan et al. | |
| 7,107,837 B2 | 9/2006 | Lauman et al. | |
| 7,153,286 B2 | 12/2006 | Busby et al. | |
| 7,297,689 B2 | 11/2007 | Miyata | |
| 7,303,541 B2 | 12/2007 | Hamada et al. | |
| 7,354,417 B1 | 4/2008 | Levin et al. | |
| 7,410,475 B2 | 8/2008 | Krensky et al. | |
| 7,421,316 B2 | 9/2008 | Gray et al. | |
| 7,507,219 B2 | 3/2009 | Noack | |
| 7,507,220 B2 | 3/2009 | Childers et al. | |
| 7,618,392 B2 | 11/2009 | Martis et al. | |
| 7,648,627 B2 | 1/2010 | Beden et al. | |
| 9,020,827 B2 | 4/2015 | Elahi et al. | |
| 2001/0040127 A1 | 11/2001 | Donig et al. | |
| 2003/0154108 A1 | 8/2003 | Fletcher-Haynes et al. | |
| 2003/0220598 A1 | 11/2003 | Busby et al. | |
| 2003/0220609 A1 | 11/2003 | Childers et al. | |
| 2004/0111293 A1 | 6/2004 | Firanek et al. | |
| 2004/0111294 A1 | 6/2004 | McNally et al. | |
| 2005/0055242 A1 | 3/2005 | Bello et al. | |
| 2005/0089994 A1 | 4/2005 | Neftel | |
| 2005/0184153 A1 | 8/2005 | Auchinleck | |
| 2005/0228300 A1 | 10/2005 | Jaime et al. | |
| 2005/0244909 A1 | 11/2005 | Hamada | |
| 2006/0089542 A1 | 4/2006 | Sands | |
| 2006/0226079 A1 | 10/2006 | Mori | |
| 2006/0241543 A1 | 10/2006 | Gura | |
| 2007/0061045 A1 | 3/2007 | Hamada et al. | |
| 2007/0106247 A1 | 5/2007 | Burnett et al. | |
| 2007/0276328 A1 | 11/2007 | Childers et al. | |
| 2008/0097283 A1 | 4/2008 | Plahey | |
| 2008/0161751 A1 | 7/2008 | Plahey et al. | |
| 2008/0183126 A1 | 7/2008 | Landherr et al. | |
| 2008/0183127 A1 | 7/2008 | Landherr et al. | |
| 2008/0200867 A1 | 8/2008 | Bedingfield | |
| 2008/0243211 A1 | 10/2008 | Cartwright et al. | |
| 2008/0281630 A1 | 11/2008 | Sekura | |
| 2009/0076856 A1 | 3/2009 | Darby et al. | |
| 2009/0095679 A1 | 4/2009 | Demers et al. | |
| 2009/0113335 A1 | 4/2009 | Sandoe et al. | |
| 2009/0119695 A1 | 5/2009 | Ramaswamy et al. | |
| 2009/0187139 A1* | 7/2009 | Mastalli .......... G16H 20/40 604/29 |
| 2009/0222119 A1 | 9/2009 | Plahey et al. | |
| 2009/0271119 A1 | 10/2009 | Hamada et al. | |
| 2009/0275881 A1 | 11/2009 | Lo et al. | |
| 2009/0275883 A1 | 11/2009 | Chapman et al. | |
| 2009/0278696 A1 | 11/2009 | Lindh et al. | |
| 2009/0294339 A1 | 12/2009 | Biewer et al. | |
| 2009/0299273 A1 | 12/2009 | Lee et al. | |
| 2009/0306573 A1 | 12/2009 | Gagner et al. | |
| 2010/0010423 A1 | 1/2010 | Yu et al. | |
| 2010/0010426 A1 | 1/2010 | Childers et al. | |
| 2010/0010427 A1 | 1/2010 | Yu et al. | |
| 2010/0010428 A1 | 1/2010 | Yu et al. | |
| 2010/0140149 A1 | 6/2010 | Fulkerson et al. | |
| 2010/0315225 A1 | 12/2010 | Teague | |
| 2011/0054352 A1 | 3/2011 | Ko et al. | |
| 2011/0054378 A1 | 3/2011 | Fulkerson | |
| 2011/0071465 A1 | 3/2011 | Wang | |

FOREIGN PATENT DOCUMENTS

| | | |
|---|---|---|
| EP | 1872814 | 1/2008 |
| EP | 2 263 524 | 12/2010 |
| EP | 3 219 340 | 9/2017 |
| JP | 2002-539896 | 11/2002 |
| JP | 2004-049497 | 2/2004 |
| JP | 2005-027886 | 2/2005 |
| JP | 2007-029705 | 2/2007 |
| JP | 2007-140775 | 6/2007 |
| JP | 2008-508934 | 3/2008 |
| WO | 00/57935 | 10/2000 |
| WO | 02080085 | 10/2002 |
| WO | 03026724 | 4/2003 |
| WO | 2003/099355 | 12/2003 |
| WO | 2007120904 | 10/2007 |
| WO | 2007/126360 | 11/2007 |
| WO | 2008/027967 | 3/2008 |
| WO | 2008/097316 | 8/2008 |
| WO | 2008/106191 | 9/2008 |
| WO | 2009094184 | 7/2009 |
| WO | 2009/134879 | 11/2009 |
| WO | 2009134881 | 11/2009 |
| WO | 2010006131 | 1/2010 |
| WO | 2010135078 | 11/2010 |
| WO | 2011046797 | 4/2011 |

OTHER PUBLICATIONS

Japanese Office Action dated Mar. 10, 2015 for related Japanese Appln. No. 2012-534235.

Rippe B. et al., "Computer Simulation of Peritoneal Fluid Transport in CAPD", Kidney International, vol. 40 (1991), pp. 315-325.

Tormey et al., "Long-term successful management of refractory congestive cardiac failure by intermittent ambulatory peritoneal ultrafiltration", Q J Med, 1996, vol. 89, pp. 681-683.

Vonesh E. F. and Rippe B., Net fluid absorption under membrane transport models of peritoneal dialysis, Blood Purif 1992; 10:209-226.

Written Opinion and International Search Report For Corresponding International Application No. PCT/US2009/042106 dated Aug. 31, 2009.

(56) References Cited

OTHER PUBLICATIONS

Written Opinion and International Search Report For Corresponding International Application No. PCT/US2009/042103 dated Aug. 31, 2009.
Written Opinion and International Search Report For Corresponding International Application No. PCT/US2010/051754 dated Mar. 20, 2011.
International Preliminary Report on Patentability for corresponding International Application No. PCT/US2010/051754 dated May 31, 2011.
European Search Report Appl. No. 17168783.3-1651 dated Jul. 27, 2017—8 pages.
Notice of Opposition—EP Patent No. 3219340, Jan. 2, 2019.
Sleep-safe; Software-Version 1.0, Fresenius Medical Care; Art. Nr. 677 804 1—151 pages.
PatientOnLine Release 4.2, User Manual, Fresenius Medical Care—302 pages.
QuickMark Mobile Barcode—Press Release; online—4 pages.
Apple—iPhone—Technical Specifications; online—3 pages.
EP Notice of Opposition Application No. 10771589.8-1115/2488227 dated Apr. 5, 2018—42 pages.
Twardowski et al., "Osmotic Agents and Ultrafiltration in Peritoneal Dialysis"; Nephron 42: pp. 93-101 (1986).
Mujais et al., "Evaluation and Management of Ultrafiltration Problems in Peritoneal Dialysis"; Peritoneal Dialysis International, Sep. 2000, vol. 20, Suppl. 4.
U.S. Appl. No. 61/252,363, filed Oct. 16, 2009—Certified Priority Document.
U.S. Appl. No. 12/826,183, filed Jun. 29, 2010—Certified Priority Document.
Japanese Office Action (with English translation) dated Jul. 26, 2016 in corresponding Japanese application No. 2015-150852 (8 pages).

* cited by examiner

OPTIMIZING PERITONEAL DIALYSIS USING A PATIENT HAND-HELD SCANNING DEVICE

PRIORITY CLAIM

This application is a continuation of U.S. patent application Ser. No. 16/658,894, filed Oct. 21, 2019, now U.S. Pat. No. 11,058,809, which is a continuation of U.S. patent application Ser. No. 14/697,022, filed Apr. 27, 2015, now U.S. Pat. No. 10,449,284, which is a continuation of U.S. patent application Ser. No. 12/826,183, filed Jun. 29, 2010, now U.S. Pat. No. 9,020,827, which claims priority to and the benefit of U.S. Provisional Patent Application Ser. No. 61/252,363, filed Oct. 16, 2009, the entire contents of each of which are hereby incorporated by reference and relied upon.

BACKGROUND

The present disclosure relates to medical fluid delivery and in particular to a peritoneal dialysis ("PD") therapy.

Due to various causes, a person's renal system can fail. Renal failure produces several physiological impairments and difficulties. The balance of water, minerals and the excretion of daily metabolic load is no longer possible and toxic end products of nitrogen metabolism (urea, creatinine, uric acid, and others) can accumulate in blood and tissue. Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life saving.

Hemodialysis and peritoneal dialysis are two types of dialysis therapies used commonly to treat loss of kidney function. A hemodialysis ("HD") treatment utilizes the patient's blood to remove waste, toxins and excess water from the patient. The patient is connected to a hemodialysis machine and the patient's blood is pumped through the machine. Catheters are inserted into the patient's veins and arteries so that blood can flow to and from the hemodialysis machine. The blood passes through a dialyzer of the machine, which removes waste, toxins and excess water from the blood. The cleaned blood is returned to the patient. A large amount of dialysate, for example about 120 liters, is consumed to dialyze the blood during a single hemodialysis therapy. Hemodialysis treatment lasts several hours and is generally performed in a treatment center about three or four times per week.

Peritoneal dialysis uses a dialysis solution, also called dialysate, which is infused into a patient's peritoneal cavity via a catheter. The dialysate contacts the peritoneal membrane of the peritoneal cavity. Waste, toxins and excess water pass from the patient's bloodstream, through the peritoneal membrane and into the dialysate due to diffusion and osmosis, i.e., an osmotic gradient occurs across the membrane. The spent dialysate is drained from the patient, removing waste, toxins and excess water from the patient. This cycle is repeated.

There are various types of peritoneal dialysis therapies, including continuous ambulatory peritoneal dialysis ("CAPD"), automated peritoneal dialysis ("APD"), tidal flow APD and continuous flow peritoneal dialysis ("CFPD"). CAPD is a manual dialysis treatment. The patient manually connects an implanted catheter to a drain, allowing spent dialysate fluid to drain from the peritoneal cavity. The patient then connects the catheter to a bag of fresh dialysate, infusing fresh dialysate through the catheter and into the patient. The patient disconnects the catheter from the fresh dialysate bag and allows the dialysate to dwell within the peritoneal cavity, wherein the transfer of waste, toxins and excess water takes place. After a dwell period, the patient repeats the manual dialysis procedure, for example, four times per day, each treatment lasting about an hour. Manual peritoneal dialysis requires a significant amount of time and effort from the patient, leaving ample room for improvement. There is room for improvement in the selection of dwell times for each patient.

Automated peritoneal dialysis ("APD") is similar to CAPD in that the dialysis treatment includes drain, fill, and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysate and to a fluid drain. APD machines pump fresh dialysate from a dialysate source, through the catheter, into the patient's peritoneal cavity, and allow the dialysate to dwell within the cavity, and allow the transfer of waste, toxins and excess water to take place. The source can be multiple sterile dialysate solution bags.

APD machines pump spent dialysate from the peritoneal cavity, though the catheter, to the drain. As with the manual process, several drain, fill and dwell cycles occur during APD. A "last fill" occurs at the end of CAPD and APD, which remains in the peritoneal cavity of the patient until the next treatment. Both CAPD and APD are batch type systems that send spent dialysis fluid to a drain. Tidal flow systems are modified batch systems. With tidal flow, instead of removing all of the fluid from the patient over a longer period of time, a portion of the fluid is removed and replaced after smaller increments of time.

Continuous flow, or CFPD, systems clean or regenerate spent dialysate instead of discarding it. These systems pump fluid into and out of the patient, through a loop. Dialysate flows into the peritoneal cavity through one catheter lumen and out another catheter lumen. The fluid exiting the patient passes through a reconstitution device that removes waste from the dialysate, e.g., via a urea removal column that employs urease to enzymatically convert urea into ammonia. The ammonia is then removed from the dialysate by adsorption prior to reintroduction of the dialysate into the peritoneal cavity.

In each of the kidney failure treatment systems discussed above, it is important to control ultrafiltration, which is the process by which water (with electrolytes) moves across a membrane, such as a dialyzer or peritoneal membrane. For example, ultrafiltration in peritoneal dialysis is a result of transmembrane and osmotic pressure differences between blood and dialysate across the patient's peritoneal membrane. It is also important to control the concentration of metabolic substances in the patient's bloodstream, such as urea concentration, $\beta_2$-microglobulin, creatinine concentration, and so forth. Each of these, along with many other variables, constitutes a peritoneal dialysis outcome.

Each patient is different, possessing for instance, a unique peritoneal membrane, its own separation characteristics, and its unique response to peritoneal dialysis. Each patient is also different with respect to body surface area ("BSA") and total body water volume, which also have an effect on transport characteristics. Each patient is different in terms of transport characteristics that relate to the ultrafiltration rate.

Each patient is also different in terms of response to dialysis, that is, the amount of water and waste removed in a given time period, using a given fill volume, a particular dialysis fluid, and so forth. What is needed is a way to better control the particular dialysis therapy offered to each patient, so that the treatment will yield the best therapy outcome for that patient, for one or more dialysis input parameters While APD frees the patient from having to manually performing the drain, dwell, and fill steps, a need still exists for CAPD. Some patients prefer the control that CAPD offers. Since the patient is awake during CAPD, the patient can adjust himself/herself during drain to produce more complete drains. Further, many patients who perform APD also perform a midday exchange using a CAPD technique.

In optimizing the therapy for both APD and CAPD, the dwell period becomes important. If spent dialysate is permitted to dwell in the patient's peritoneal cavity too long, solutes and water that have been removed from the patient into the dialysate can reenter the patient's body. It is accordingly desirable to provide an apparatus and method that prevents such a situation from occurring.

SUMMARY

The present disclosure provides a system, method and device for optimizing a peritoneal dialysis therapy and in particular a dwell period during which a dialysis fluid or solution, sometimes termed dialysate, is allowed to dwell within the patient's peritoneal cavity. As discussed in the BACKGROUND, if the dialysis fluid is allowed to dwell too long within the patient, solutes and water that the dialysis fluid has removed can reenter the patient. On the other hand, the dialysis fluid should be allowed to dwell within the patient until it is used fully or until the osmotic gradient provided by the dialysis fluid is fully spent.

The present disclosure sets forth systems, methods and apparatuses for selecting a dwell time for peritoneal dialysis based on an individual patient's response to dialysis, and also based on one or more peritoneal dialysis input parameters. The dwell time is selected to yield the maximum fluid toxin (e.g. urea, creatinine) removal for that patient based on the dialysis parameters. The embodiments set forth herein allow the optimal dwell time to be determined based on patient's transport type, gender, height, fill volume and dialysate type, for example. The system alerts the patient to the optimal dwell time. The alert signals to the patient when to drain the spent dialysate to achieve optimal clearance and ultrafiltration ("UF") removal.

The system also logs the treatment information and makes such information available to a doctor or clinician, so that (i) the effectiveness of the patient's prescription and (ii) the patient's compliance can be identified and monitored, and (iii) the patient's therapy prescription can modified if needed. In this manner, the system and method of the present disclosure optimizes the patient's treatment on a local (therapy) level and on integrated (e.g., monthly visits to doctor or clinician) level.

In one embodiment, the system includes a portable reader, such as key ring, key fob, necklace or device that can be worn on a patient, patient's belt or be carried in the patient's pocket. The portable reader includes an optical scanner, such as a barcode scanner, a wireless receiver or reader, such as a radio-frequency ("RFID") or Bluetooth™ receiver, an output device, such as an audio, visual, mechanical or audiovisual output device, processing and memory. The patient holds the portable reader next to a marking on the dialysis fluid supply container or bag. The marking can for example be a barcode or RFID tag. The barcode identifies the solution type (e.g. dextrose level and/or other chemical characteristics) and/or the solution volume. The wireless receiver of the portable reader also receives the patient's pre-therapy weight from a weigh scale configured to weigh the patient and send a weight signal, e.g., wirelessly via patient Bluetooth™ emitter to the receiver. Alternatively or additionally, wireless receiver of the portable reader also receives the patient's pre-therapy blood pressure from a blood pressure cuff or bioimpedance measurement form a bioimpedance device.

The processing and memory receive the solution and use an algorithm to determine the optimal dwell period, which the output device then communicates to the patient. For example, the portable reader can sound an alarm at the end of the dwell or count down a timer, so that the patient can know during dwell how much time remains before drain.

The processing and memory also store data for each day's treatment, such as the solution used, how many bags or total volume and pre- and post-therapy patient weight, blood pressure, blood glucose levels, and therapy dwell times. In a first primary embodiment, the patient brings the portable reader to the doctor's or clinician's office every month or periodically. At the office the data from the portable reader is downloaded to the clinician's/doctor's computer, e.g., via (i) wireless communication, in which case the portable reader also includes a wireless communication (e.g., Bluetooth™) emitter, or (ii) by plugging the portable reader into the clinician's computer, in which case the portable reader can include a connector (e.g., retractable) for a computer port (e.g., universal serial bus ("USB") port).

In a second primary embodiment, the portable reader records the dialysis solution bag and sends data wirelessly to the patient's cellular phone, personal electronic mail device or combined device (referred to herein collectively as a personal communication device ("PCD")). The weight scale sends patient weight data wirelessly to the personal communication device. The PCD includes processing and memory to calculate the optimal dwell. The cellular phone can notify the patient when it is time for drain or send a signal back to the portable reader to alert the patient as described above. In a variation of this second embodiment, the portable reader accepts both solution and weight scale data and stores the algorithm necessary to determine the optimal dwell. The portable reader sends appropriate data wirelessly to the PCD. The PCD downloads the appropriate data to the doctor's/clinician's computer and/or to a supply ordering service on a periodic basis, e.g., daily, for patient therapy tracking. Communication between the personal communication device and the doctor's/clinician's computer can be via satellite, e.g., via text message.

In a third primary embodiment, a base station replaces the PCD of the second primary embodiment. Again, the weight scale data, blood pressure, and blood glucose levels can be sent wirelessly to the base station or to the portable reader. One of the base station or the portable reader includes processing and memory configured to determine the optimal dwell time. In one embodiment, the base station signals the portable reader to alert the patient of the optimal dwell time. The base station communicates the appropriate data to the doctor's/clinician's computer periodically, e.g., daily. Communication between the base station and the doctor's/clinician's computer and, if desired, a supply ordering service, can be via an internet connection. The base station can also serve to charge the portable reader, and thus it is contemplated to have communication between the portable reader and the base station be via direct computer, e.g., via USB link.

In a fourth primary embodiment, the patient's PCD replaces the portable scanner of the first three primary embodiments. The personal communication device uses a built-in camera to (i) scan the bag marking and (ii) receive weigh scale data, blood pressure, blood glucose level, bioimpedance measurement, e.g., wirelessly. The PCD communicates the optimal dwell or start drain time to the patient by sounding an alarm, vibrating, providing a visual countdown or some combination thereof. The personal communication device sends therapy log information to the doctor's/clinician's computer and/or a supply ordering service, e.g., via satellite communication, e.g., daily.

It is contemplated that the systems and methods described herein be used with automated peritoneal dialysis ("APD"), however, APD machines typically control the dwell time and begin drain automatically. The therapy login feature is still applicable however, and, many patients who use APD still perform midday exchanges, for which optimal dwell times can be controlled as described above. Moreover, peritoneal dialysis or continuous ambulatory peritoneal dialysis ("CAPD") is still used by many patients and is one primary modality envisioned for the systems and methods herein described. If the CAPD therapy uses multiple bags, it is contemplated that the patient scan each bag prior to use to ensure that the proper bag is matched with the proper dwell time.

The present disclosure also includes multiple embodiments for therapy downloading and supply ordering systems and methods. Here, the doctor, nurse or clinician can determine a preferred therapy prescription for the patient and send the prescription to the server. The server manipulates the selected prescription into a bill of lading having the requisite supplies, e.g., solution type and volume amount, to enable patient 12 to perform the prescribed therapy. The server sends the bill of lading to a warehouse computer of a warehouse storing the supplies. A delivery person receives the supplies from the warehouse and delivers the supplies to the patient. The patient in turn uses one of the communication devices described herein to inform the server as to how many of the patient's stock of supplies have been used. This feedback of supply consumption information from the patient to the server enables the server to generate the bill of lading so as to only deliver the solution bags and other supplies that the patient actually needs before the next delivery is made.

The server knowing the amount of supplies that the patient has actually used also allows the doctor, nurse or clinician to access the feedback data from the patient to evaluate the patient's compliance with the prescribed therapy. In a slight alternative embodiment, the delivery person also has a communication device that is used to communicate with the server the amount of supplies that are actually delivered to the patient.

It is accordingly an advantage of the present disclosure to optimize peritoneal dialysis ("PD") dwell times.

It is a further advantage of the present disclosure to provide a convenient and portable device that enables a patient to optimize his/her PD therapy.

It is another advantage of the present disclosure to provide therapy log data to a doctor or clinician to optimize a PD therapy over a longer term.

It is yet another advantage of the present disclosure that supply ordering can be automated via a periodic communication of dialysate consumption to a supply ordering and inventory tracking system.

It is still a further embodiment of the present disclosure to be able to readily monitor the patient's compliance with prescribed therapy.

Additional features and advantages are described herein, and will be apparent from the following Detailed Description and the figures.

DETAILED DESCRIPTION

Figure 1A:
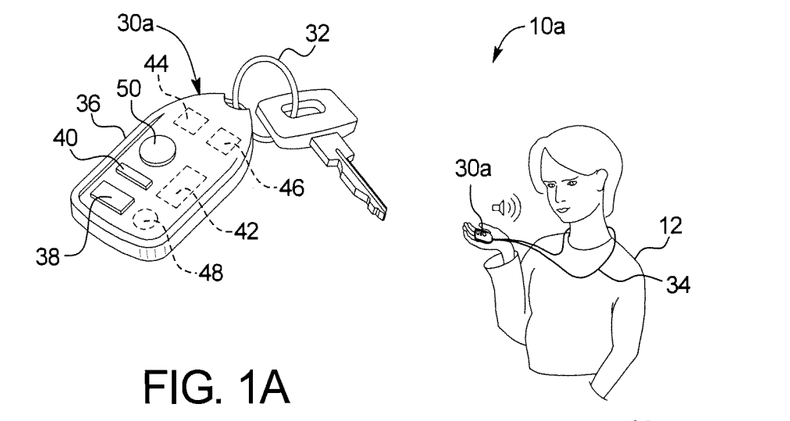
FIG. 1A is a schematic illustration of one embodiment of a local therapy optimization system and method of the present disclosure.

Referring now to the drawings and in particular to FIG. 1, one embodiment of the therapy optimization system and method is illustrated by system 10a. System 10a involves the interaction between a patient 12 and a doctor, nurse or clinician 14 (referred to herein collectively as medical professional 14). In any of the systems discussed herein, the patient performs a peritoneal dialysis ("PD") treatment, which can be an automated peritoneal dialysis ("APD") therapy or a manual PD therapy, which is sometimes called a continuous ambulatory peritoneal dialysis ("CAPD"). APD typically programs automated dwell times, such that the patient drains occur automatically, enabling the patient to sleep through the bulk of the PD therapy. Nevertheless, many APD treatments also involve midday exchanges that can take advantage of systems and associated methodology set forth herein. Even for the automated night exchanges, however, APD patients can use the information log features set forth herein. Certainly, the systems set forth herein are entirely applicable to CAPD.

Regardless of whether APD or CAPD is used, the PD treatment typically involves one or more bags or containers 16 of fresh dialysate. Bagged dialysate can be provided in different varieties. For example, the assignee of the present disclosure markets bagged dialysate under the trade names Dianeal™, Dianeal-N™, Physioneal™, Extraneal™, and Nutraneal™. The dialysates differ in chemical composition and in particular dextrose level. A higher dextrose level dialysate pulls more water or ultrafiltration ("UF") off of the patient. The higher dextrose level dialysate, however, has a higher caloric content, such that a balance is typically struck for the patient between how much effluent water the patient needs to remove over the treatment versus how much weight gain the patient may incur due to the dextrose level.

Dialysate container 16 can also vary in volume, such as being provided in one, 1.5, two, and 2.5 liter bags. Dialysate container 16 can be completely premixed in a single chamber or be separated into components in a dual or multi-chamber bag separated by a seal that patient 12 breaks to mix the components prior to treatment. All of the above variables, including chemical composition, dextrose level and container volume affect how long the dialysate should optimally be allowed to dwell within the patient. That is, a higher dextrose level dialysate should be allowed to reside longer within the patients peritoneum to use its full osmotic potential. Also, a larger volume of fresh dialysate will also have more potential to remove solutes and excess water, and therefore should be allowed to remain in the patient's peritoneum longer.

Dialysate container or bag 16 can be provided accordingly with a marker or barcode 18, which designates at least one of dialysate composition, dextrose level and container solution volume. System 10a also includes a patient scale 20, which the patient uses to weigh himself or herself. The tracking of the patient's weight assists the physician in monitoring the patient's weight trends, which may result in a prescription change, for example if the patient appears to be gaining weight from the therapy. Scale 20 is included with electronics in and particular a wireless emitter 22 for emitting a signal indicative of the weight of patient 12. One suitable scale having a wireless output and system for addressing and accessing same is disclosed in U.S. patent application Ser. No. 12/469,371 ("'371 application"), now U.S. Pat. No. 8,282,829, entitled "System and Method for Automated Data Collection of 24 Hour Ultrafiltration and Other Patient Parameters Using Wired or Wireless Technology", filed May 20, 2009, assigned it to the assignee of the present disclosure, the entire contents of which are incorporated by reference herein and relied upon. Wireless emitter 22 may use a known wireless communication technology, such as Bluetooth™, ZigBee™, or other protocol, e.g., one based on IEEE 802.

System 10a further includes a portable reader 30a, which can be formed as a key ring 32 or worn on a necklace 34. Portable reader 30a includes a housing 36, which can be formed via plastic injection molding. Housing 36 houses an optical scanner 38, such as a laser scanner, which reads marking or barcode 18 placed on solution bag or container 16. In one embodiment, when patient 12 holds portable reader 30a close enough to marking 18, patient 12 presses an input device 40, which causes scanner 38 to read marking 18. Alternatively, scanner 38 reads marking 18 automatically when marking 18 is within range of portable reader 30a.

Portable reader 30a also includes a wireless receiver 42, which accepts a wireless weight signal from wireless emitter 22 of weight scale 20. One suitable protocol and addressing system for enabling wireless receiver 42 to accept a weight signal from wireless emitter 22 is discussed above in the '371 application.

Housing 36 of portable reader 30a is further fitted with processing 44 and memory 46, which receive and store the marking information from scanner 38. Processing 44 and memory 46 are configured to in turn look-up and store solution data (e.g., chemical composition, dextrose level and volume) that is particular to a particular marking or barcode 18. Processing 44 and memory 46 are further configured to accept the weight data received at wireless receiver 42 and store such data in memory 46.

Processing 44 and memory 46 store an algorithm that uses the solution data and the patient specific data to determine an optimal dwell time for patient 12 using fresh dialysate from container 16. One suitable algorithm for determining the optimal dwell time is to generate a patient specific time to achieve maximum ultrafiltration, urea removal or creatinine removal. All fluid and toxin (urea and creatinine) vs. dwell time curves have a maximum value at a certain dwell time. The curves can be generated from kinetic modeling (e.g. using PD Adequest™ provided by the assignee of the present disclosure) by varying patients' transporter types, body surface area, type of solution, and fill volume. The maximum fluid and toxin removal values and related optimum dwell times can be recorded in look-up tables and are stored in memory 46 that cross references patient gender, weight (for calculating body surface area), fill volume, type of transporter and type of solution. Suitable algorithms for determining optimal dwell times is disclosed in copending U.S. patent application Ser. No. 12/431,458, U.S. Publication No. 2009/0275881, entitled, "Optimizing Therapy Outcomes For Peritoneal Dialysis", filed Apr. 28, 2009, assigned to the assignee of the present disclosure, the entire contents of which are incorporated herein by reference and relied upon.

Housing 36 of portable reader 30a is further outfitted with an output device 48, such as an audio output, a light or flashing light (e.g., light emitting diode ("LED")) or display, such as a liquid crystal display ("LCD"). Output device 48 communicates the optimal dwell time determined by processing 44 and memory 46 to the patient 12. Communication of the optimal dwell time can be via an alert or alarm when dwell has been completed. Alternatively, a display, e.g., LCD display, shows a countdown of remaining dwell time, such that patient 12 can gage how long the current dwell is from completion. It is contemplated for device 48 (for this and any of the embodiments discussed herein) to communicate information visually, audibly, tactilely and any combination thereof.

In one embodiment, processing 44 and memory 46 determine a dwell duration. It is therefore necessary to know when the beginning of dwell occurs, so that a clock or timer can begin to run. In one embodiment, housing 36 of portable reader 30a includes a start dwell input device 50, which communicates electrically with processing 44, and which patient 12 presses as soon as filling from dialysate container 16 to the patient's peritoneum has been completed. Pressing input device 50 signals to processing 44 and memory 46 that the dwell has begun. A timer or counter then begins to run, and output device 48 is activated to show a count down and/or is activated upon completion of the optimized dwell to inform the patient to begin draining the spent dialysis fluid form the patient's peritoneal cavity.

The PD therapy, and in particular a CAPD therapy, may involve the patient connecting to and disconnecting from multiple containers 16 of fresh dialysate manually. It is contemplated in one embodiment to have patient 12 read the appropriate marking 18 of each container 16 of dialysate just before that container is to be used. In this way, the optimal dwell time is determined and known for each container 16 just prior to its use. It is also contemplated, especially in instances in which the same dialysate type and volume is to be used multiple times in the same therapy, to enable patient 12 to scan each container 16 at the beginning of therapy, such that the patient does not have to scan a container 16 between each fill. It is quite likely than that the optimal dwell time will be the same for each container 16, such that patient 12 does not have to keep track of which container 16 has been scanned first, second, third, and so on. If containers 16 contain different types or volumes or fresh dialysate, portable reader 30a can determine same and inform the patient that a particular container 16 needs to be used in the order in which it has been scanned.

In one embodiment, patient 12 weights himself or herself on scale 20 prior to each fill and weighs the drain volume. From these data, UF trending can be done for both CAPD and APD patients. Using the UF trending, clinicians may check the patients compliance and potentially change solution to optimize the therapy such that the algorithm used in processing 44 and of memory 46 begins with a most current patient weight in determining the optimal dwell just prior to each patient fill.

In an alternative embodiment in which patient 12 is not able to scan multiple containers 16 at the beginning of therapy, the patient's weight loss after each patient drain can be estimated using another algorithm, such that a new weight can be entered for each optimized dwell calculation or determination. The algorithm can for example use a certain percentage of the fill volume as the estimated UF removed over that cycle. For example, the percentage can be eight percent of the fill volume. The percentage is in one embodiment determined on a patient specific basis.

Instead of a separate algorithm, processing 44 and memory 46 can further alternatively estimate or empirically determine the weight loss of the patient given the patient's beginning weight, total target weight loss, solution type and volume used over the previously optimized dwell time.

Figure 1B:
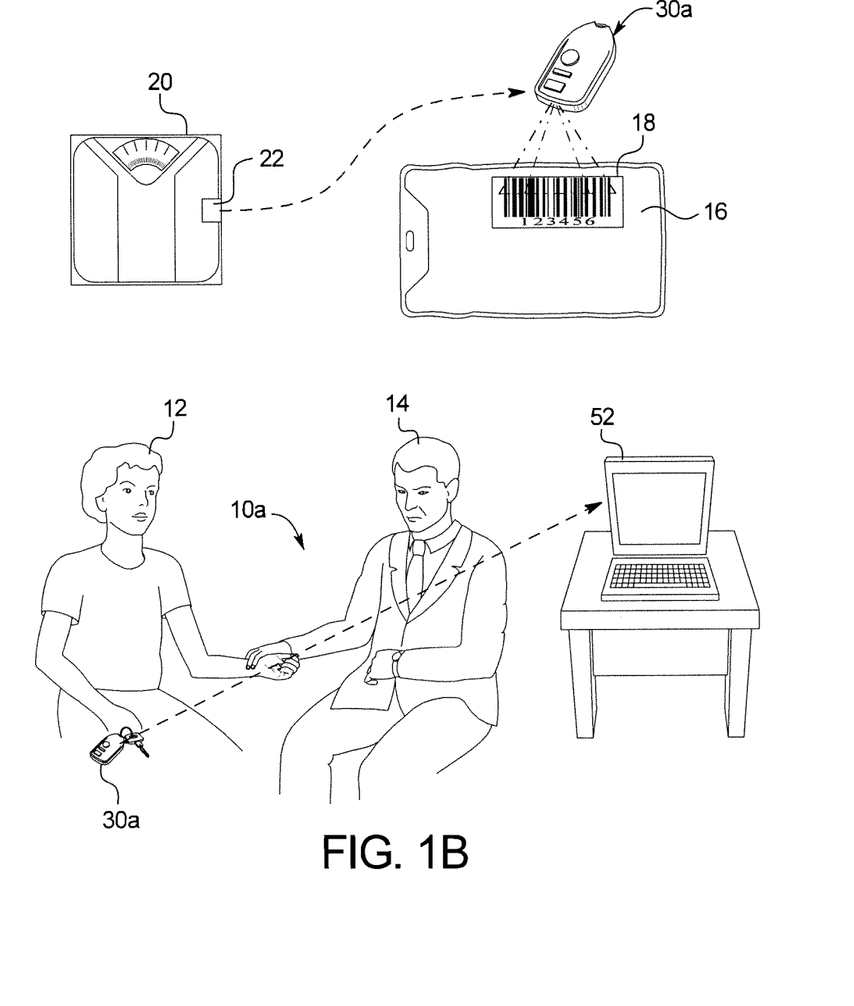
FIG. 1B is a schematic illustration of one embodiment of an integrated therapy optimization system and method of the present disclosure.

Referring now to FIG. 1B, one embodiment for downloading logged information from portable reader 30a of system 10a to a medical professional 14 for long term therapy optimization is illustrated. In one implementation, wireless receiver 42 is a wireless transceiver, e.g., using Bluetooth™, ZigBee™, or other wireless protocol, e.g., based on IEEE 802, which not only receives wireless information but also transmits wireless information. In the illustrated embodiment, patient 12 brings portable reader 30a to the office of the medical professional 14. As soon as portable reader 30a is placed within wireless communication range of the medical professional's computer 52, portable reader 30a automatically downloads the information read from weight scale 20, solution container 16 and information determined at portable reader 30a for each container used over a period of time, such as a month or whatever the period exists between visits to medical professional 14.

In a further implementation, portable reader 30a includes a connector (not shown). In the operational position, the connector can be plugged into a port, such as a universal serial bus ("USB") port, of the medical professional's computer 52. The above described information is then downloaded to the computer. Once on the computer, medical professional 14 can review the results and change the patient's therapy prescription if needed. FIGS. 1A and 1B for system 10a accordingly illustrate that system 10a optimizes therapy on a local or daily basis and over an integrated basis spanning a period of time. It should be appreciated that in the illustrated embodiment, communication in system 10a takes place wirelessly over a local wireless network, both in the environment of patient 12 and medical professional 14 (which can alternatively be local wired communication).

Figure 2:
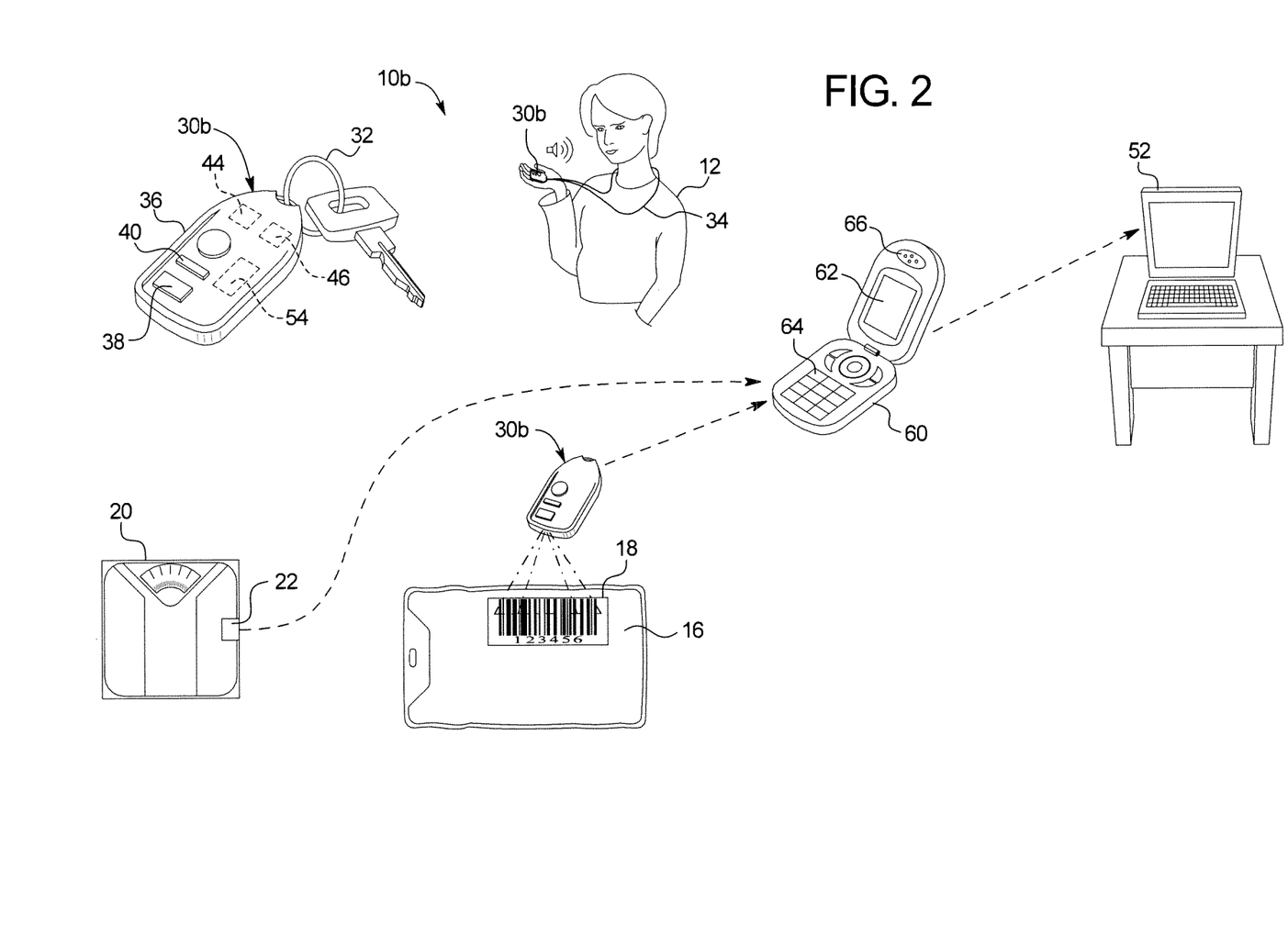
FIG. 2 is a schematic illustration of a second embodiment of a local therapy optimization system and method of the present disclosure.

Referring now to FIG. 2, an alternative system 10b is illustrated. System 10b includes many of the features of system 10a, which are numbered the same accordingly, such as scale 20 having wireless emitter 22, solution container 16 having marking or barcode 18 and medical professional computer 52. An alternative portable reader 30b is provided, which can again be provided on a key ring 32, as a key fob and/or worn on a necklace 34 on patient 12.

Portable reader 30b includes scanner 38 that reads marking 18 either automatically or upon an activation of input 40, as described above. In one implementation, portable reader 30b includes processing 44 and memory 46, which again are housed in housing 36. In one implementation, local wireless receiver or transceiver 42 is replaced with a local wireless emitter 54, which can be the same or similar to emitter 22 located within scale 20. Emitter 22 sends a wireless weight signal to the patient's cellular phone or portable email device (referred to herein and collectively as a personal communication device ("PCD")) 60. Likewise, wireless emitter 54 of portable reader 30b emits a wireless signal representing solution data, as described above, to PCD 60. PCD 60 can be configured to calculate the optimal dwell time using the above described algorithm or via an empirical method. PCD 60 includes a display device 62, multiple input devices 64 and a speaker 66. One or both of video screens 62 and speaker 66 can be used as an output device, which communicates the optimal dwell time to patient 12. For example, display 62 can show a countdown of the optimal dwell time to patient 12, so that the patient knows how much longer the optimized dwell will continue. Alternatively or additionally, PCD 60 calls patient 12 via speaker 66 when it is time for the patient to drain the spent dialysate at the end of the optimized dwell period. In an alternative implementation, wireless emitter 54 is a wireless transceiver, which can receive a wireless signal from PCD 60, telling portable reader 30b to provide an audible and/or visual output to patient 12.

In yet another alternative embodiment, portable reader 30a (shown and described in connection with FIG. 1A) is used with system 10b instead of portable reader 30b. All of the optimal dwell time computations are then performed on portable reader 30a, which then sends the optimal dwell time and any other desired information to PCD 60 for communication with the medical professional's computer 52.

System 10b, like system 10a also provides a long term therapy optimization feature, which involves communication between PCD 60 and medical professional's computer 52. In an embodiment, on a periodic basis, such as daily or otherwise according to an application stored on PCD 60, PCD 60 sends a text or satellite message to the medical professional's computer 52, downloading any of the pertinent data described above in connection with system 10a. The information allows medical professional 14 to evaluate the patient's therapy performance over time and make PD prescription changes if necessary. It is therefore contemplated that the portable reader 30b communicates with PCD 60 on a first periodic basis, e.g., after each reading taken by reader 30b, and that PCD 60 communicates with the medical professional's computer 52 on a second periodic basis, e.g., daily.

Figure 3:
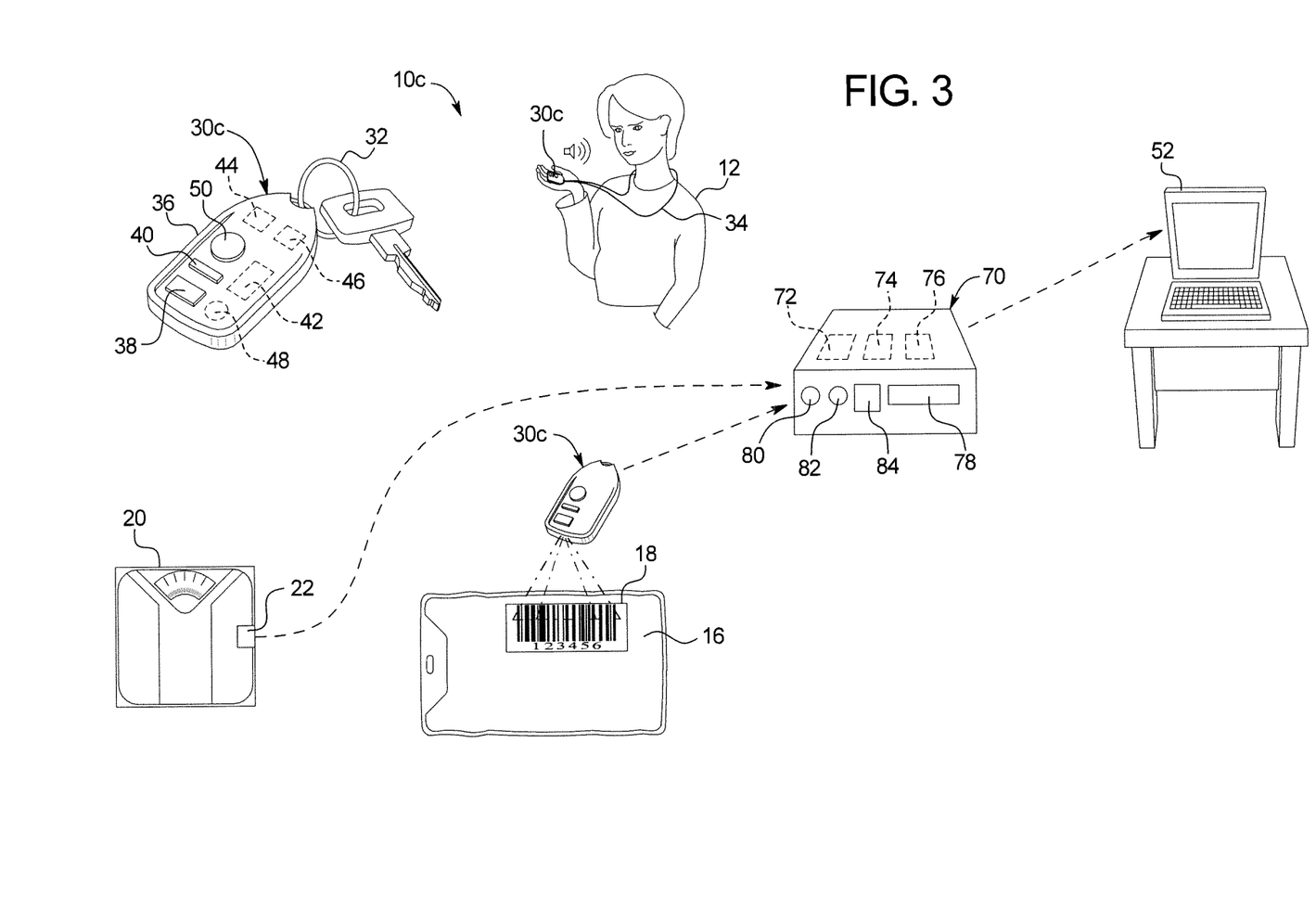
FIG. 3 is a schematic illustration of a third embodiment of a local therapy optimization system and method of the present disclosure.

Referring now to FIG. 3, an alternative system 10c is illustrated. System 10c includes many of the features of systems 10a and 10b, which are numbered the same accordingly, such as scale 20 having wireless emitter 22, solution container 16 having marking or barcode 18 and medical professional computer 52. Portable reader 30a is provided, which can again be provided on a key ring 32, as a key fob and/or worn on a necklace 34 on patient 12. As before, portable reader 30a includes scanner 38 that reads marking 18 either automatically or upon an activation of input 40, as described above. Portable reader 30a is shown here including processing 44 and memory 46, which again are housed in housing 36, however, processing 44 and memory 46 may not be needed because the dwell calculations are done at base station 70 discussed below. Portable reader 30a includes local wireless transceiver 42, to receive optimal dwell information from base station 70 for communication to patient via output device 48.

Base station 70 includes a wireless transceiver 72, which receives a wireless weight signal from transmitter 22 of weight scale 20 and any of the above-described solution data from transceiver 42 of portable reader 30a. Wireless transceiver 72 communicates dwell data to wireless transceiver 42 of portable reader 30a to provide an audible and/or visual output to patient 12.

Base station 70 includes processing 72 and memory 74 configured to calculate the optimal dwell time using the above described algorithm or via an empirical method. Base station 70 can include a display device 78, multiple input devices 80, and a speaker 82 if needed. One or both of video screens 78 and speaker 82 can be used, in addition to out device 48 of portable reader 30a, as an output device to communicate the optimal dwell time to patient 12. For example, device 48 and display 78 can show a countdown of the optimal dwell time to patient 12, so that the patient knows how much longer the optimized dwell will continue. Alternatively or additionally, speaker 82 and/or device 48 alerts patient 12 when it is time for the patient to drain the spent dialysate at the end of the optimized dwell period.

Base station 70 also includes a docking area 84 for holding portable reader 30a, charging portable reader 30a, and possibly downloading information from and importing information to portable reader 30a, such that transceiver 42 of portable reader 30a may be replaced with a USB or other type of connector that is received by a data communication port at docking area 84 of base station 70.

System 10c, like systems 10a and 10b also provides a long term therapy optimization feature, which involves communication between base station 70 and medical professional's computer 52. In an embodiment, on a periodic basis, such as daily or otherwise according to an application stored on base station 70, base station 70 sends a communication, e.g., via an internet connection, to the medical professional's computer 52, downloading any of the pertinent data described above in connection with system 10a. The information allows medical professional 14 to evaluate the patient's therapy performance over time and make PD prescription changes if necessary. It is therefore contemplated that the portable reader 30a communicates with base station 70 on a first periodic basis, e.g., after each reading taken by reader 30a, and that base station 70 communicates with the medical professional's computer 52 on a second periodic basis, e.g., daily.

Figure 4:
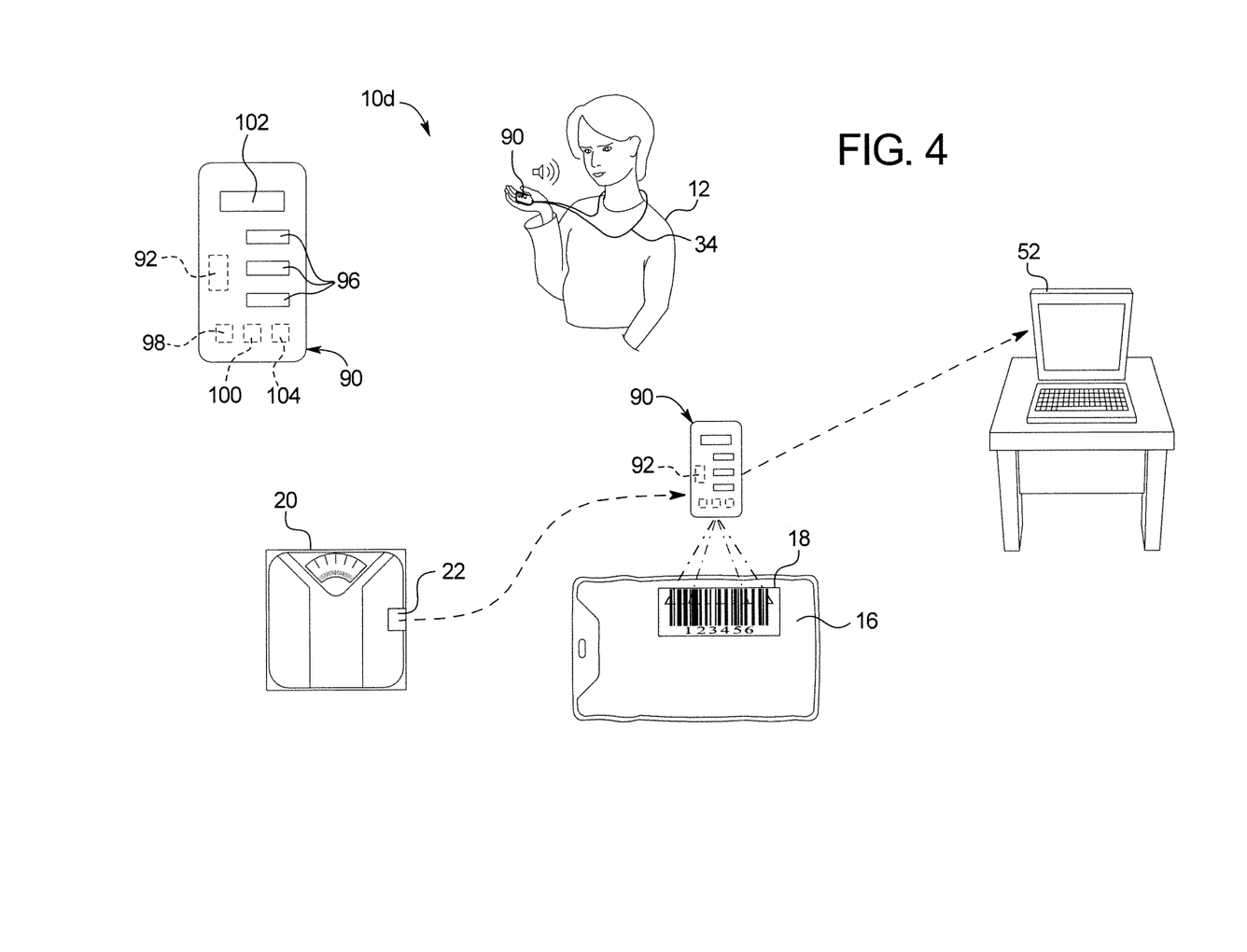
FIG. 4 is a schematic illustration of a fourth embodiment of a local therapy optimization system and method of the present disclosure.

Referring now to FIG. 4, an alternative system 10d is illustrated. System 10d includes many of the features of systems 10a, 10b and 10c, which are numbered the same accordingly, such as scale 20 having wireless emitter 22, solution container 16 having marking or barcode 18 and medical professional computer 52. personal communication device ("PCD") 90 is provided, which can be worn on a necklace 34 on patient 12 but is most likely carried by the patient. Here, PCD 90 includes a camera 94 that takes a picture of marking 18 either automatically or upon an activation of an input 96. PCD 90 in one embodiment is a smart phone, such as a iphone™, Blackberry™ or other similar device which can have electronic mail and store various software applications. PCD includes a local wireless transceiver 92 to received a wireless weight signal from transmitter 22 of weight scale 20. PCD 90 includes processing 98 and memory 100 that are configured to run software that converts the barcode picture into digital data.

One suitable software is QuickMark, provided by SimpleAct, Inc., 6F., No. 24, Cingchen St., Songshan District, Taipei City, 105 Taiwan (R.O.C.), Telephone No. 886-2-87706690. The software uses the digital data in a look-up table to determine any of the solution information described above, such and type, volume, dextrose level, and chemical concentration. Processing 98 and memory 100 as further configured to calculate the optimal dwell time using the above described algorithm or via an empirical method using the patient weight and solution data.

PCD 90 includes a display device 102, multiple input devices 96, and a speaker 104 if needed. One or both of video screen 102 and speaker 104 can be used as an output device to communicate the optimal dwell time to patient 12. For example, display 102 can show a countdown of the optimal dwell time to patient 12, so that the patient knows how much longer the optimized dwell will continue. Alternatively or additionally, speaker 104 alerts patient 12 when it is time for the patient to drain the spent dialysate at the end of the optimized dwell period.

System 10d, like systems 10a to 10c also provides a long term therapy optimization feature, which involves communication between PCD 90 and medical professional's computer 52. In an embodiment, on a periodic basis, such as daily or otherwise according to an application stored on PCD 90, PCD 90 sends a communication, e.g., via a satellite text protocol, to the medical professional's computer 52 and/or supply reordering system, downloading any of the pertinent data described above in connection with system 10a. The information allows medical professional 14 to evaluate the patient's therapy performance over time and make PD prescription changes if necessary. System 10d is desirable in one respect because a separate portable reader is not needed. PCD 90, which patient 12 uses for other purposes, such as personal email, phone usage, media storage, is also used for the optimization of the patient's dialysis therapy.

Figure 5:
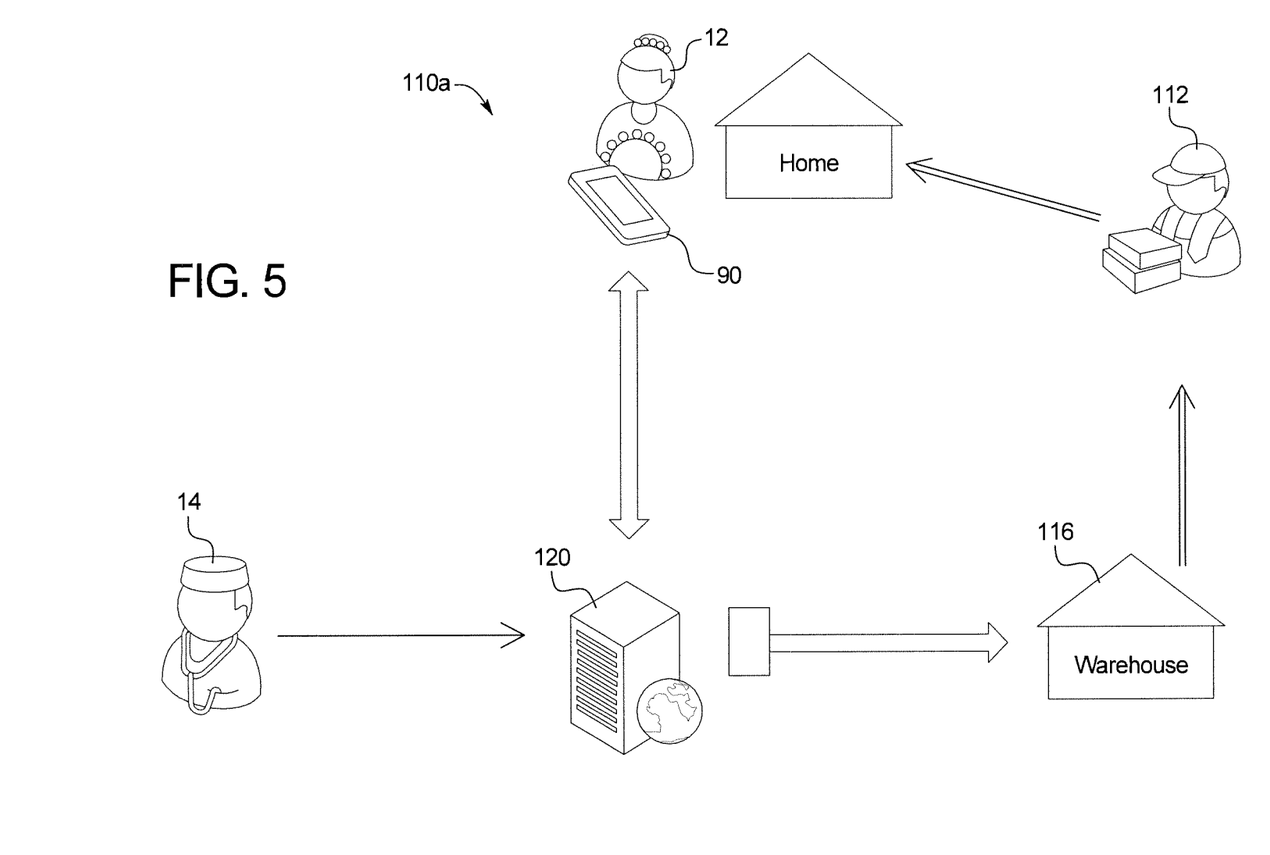
FIG. 5 is a schematic illustration of one embodiment of a therapy prescription downloading and ordering system and method of the present disclosure.

Referring now to FIG. 5, system 110a illustrates one suitable therapy prescription downloading and supply ordering system using PCD 60, PCD 90 or portable reader 30a, 30b or 30c discussed above. In the illustrated embodiment PCD 90 is shown, which includes all of the features and alternatives discussed above for PCD 90. In a first step of the method or facet of system 110a, medical professional 14 communicates with central server 120, e.g., via a web browser and computer. Server 120 can be a server maintained by the company that provides solution bags 16 or by a company contracted by the solution bag company. Medical professional 14 enters patient specific information, such as gender, height, weight, transport type, and fill volume, into the doctor's web browser located at computer 52, which can run a therapy prediction software, such as one described in U.S. patent application Ser. No. 12/170,184, entitled, "Dialysis System Having Regimen Generation Methodology", filed Jul. 9, 2008, assigned to the assignee of the present disclosure, the entire contents of which are incorporated herein by reference. The prediction software presents medical professional 14 with one or more recommendations for a therapy prescription. The software allows the medical professional 14 to accept or modify the prescription. Medical professional 14 issues a "program" command via the browser, which causes server 120 to automatically and remotely program PCD 90 with the desired therapy prescription. The communication from PCD 90 to server 120 can be a one time communication or communication that occurs periodically after medical professional 14 reevaluates patient 12.

In a second step of the method or facet of system 110*a*, server 120 communicates the medical professional's 14 prescription to a warehouse computer 116 located at a warehouse of the manufacturer of the solution and solution bags 16. The communication from server 120 to warehouse computer 116 can be transparent or done automatically whenever medical professional 14 changes the therapy prescription for patient 14. Warehouse computer 116 generates a supply order, e.g., a bill of lading.

In a third step of the method or facet of system 110*a*, warehouse computer 116 sends or prepares the bill of lading to/for delivery person 112, which is done on a periodic basis, such as once a month. In a fourth step of the method or facet of system 110*a*, delivery person 112 obtains the necessary supplies, e.g., solution bags 16, connectors, etc., and delivers the supplies to patient 12, which is also done on a periodic basis, such as once a month. It should be appreciated that steps one to four allow central server 120 to track the amount of supplies delivered from warehouse 116.

In a fifth step of the method or facet of system 110*a*, patient 12 uses PCD 90 to scan barcodes off of solution bags 16. PCD 90 receives patient data for patient 12, such as patient weight, blood pressure and blood glucose levels, as discussed above. At one or more, e.g., predetermined or patient selected time of the day, PCD 90 communicates the bag scan (or other supply usage data) and patient data to a central server 120. The communication from PCD 90 to server 120 is in one embodiment automatic and transparent to patient 12. It should be appreciated that step five allows server 120 to know how much of the supplies or solution bags 16 delivered to patient 12 have actually been used by the patient. Knowing how many supplies have been delivered from the warehouse housing computer 116 and how many supplies have been used by patient 12, system 110*a* at server 120 can determine when to deliver and how many supplies or solution bags 16 to deliver to patient 12. And as discussed, server 120 orders supplies or patient 12 based on the therapy prescription sent from medical professional 14.

Knowing how many supplies have been used by patient 12 also enables medical professional 14 to track the patient's compliance with the prescribed therapy. If patient 12 is supposed to use twenty solution bags 16 of dialysate per week, but PCD 90 consistently reports back that the patient is using less than twenty bags, medical professional 14 upon viewing this compliance data, e.g., at computer 52, can contact patient 12 to inquire as to why the patient's prescription is not being followed. Or, the compliance data can be discussed the next time patient 12 visits medical professional 14. To this end, it is contemplated for medical professional 14 to be able to access patient therapy compliance data from server 120 and/or for server 120 to periodically send patient therapy compliance data reports to computer 52 of medical professional 14. The report in one embodiment is copied to PCD 90 and patient 12, so that patient 12 knows that medical professional 14 is seeing the patient's compliance reports, good or bad.

Figure 6:
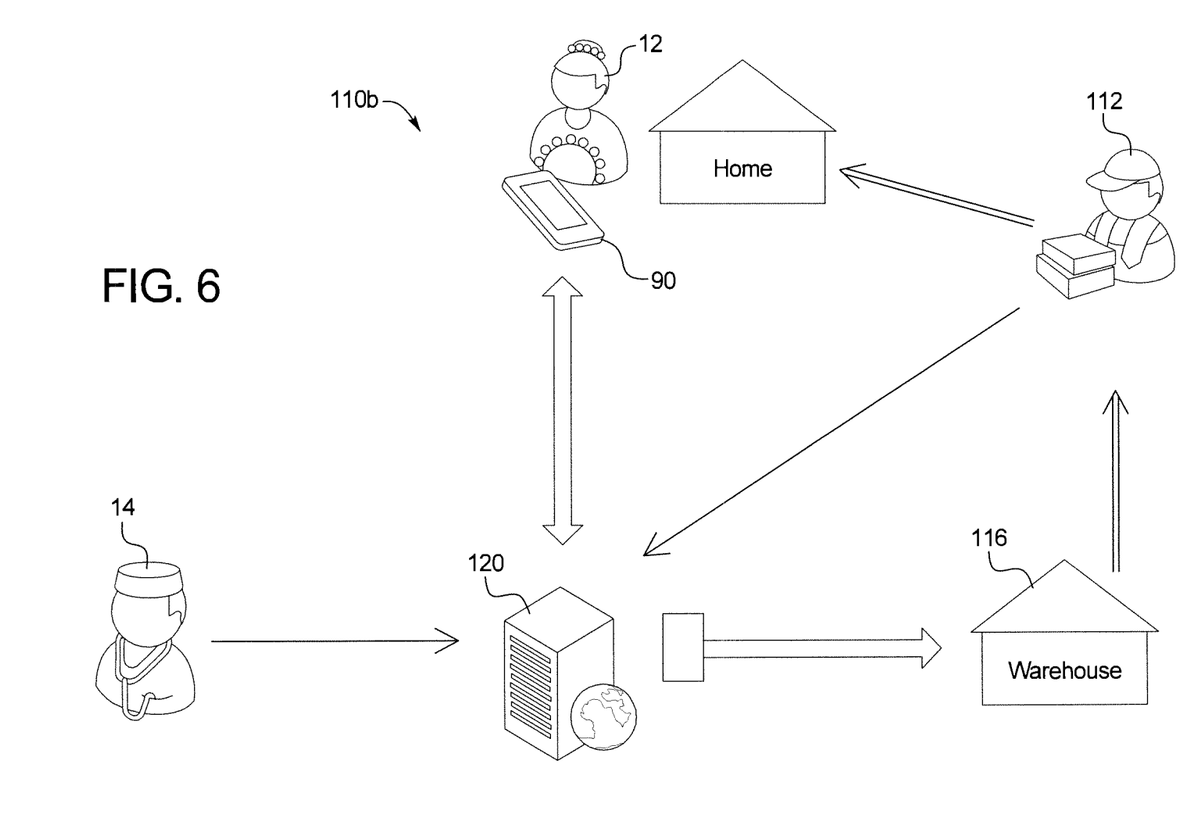
FIG. 6 is a schematic illustration of a second embodiment of a therapy prescription downloading and ordering system and method of the present disclosure.

Referring now to FIG. 6, system 110*b* illustrates another suitable therapy prescription downloading and supply ordering system using PCD 60, PCD 90 or portable reader 30*a*, 30*b* or 30*c* discussed above. System 110*b* includes all of the steps and alternatives discussed above for system 110*a* of FIG. 5. In an additional step or facet of system 110*b*, delivery person 112 is provided with a handheld device, such as PCD 60 or PCD 90, which enables delivery person 112 to report back to server 120 how many supplies, such as supply bags 16, have actually been delivered to patient 12. System 110*b* closes the loop between server 120, warehouse computer 116 and driver 112. Unlike system 110*a*, which assumes all supplies listed on the bill of lading are delivered to patient 12, system 110*b* allows server 120 to receive the amount of supplies actually delivered from delivery person 112 to patient 12. This information in combination with the amount of supplies used sent from patient PCD 90 enables server 120 to know when and how many supplies, such as solution bags 16 to order for the patient 12.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A handheld personal communication apparatus for a continuous ambulatory peritoneal dialysis ("CAPD") treatment, the apparatus comprising:
   a reader configured to read markings displayed on dialysis fluid containers to acquire data concerning at least one of a dialysis fluid type or a dialysis fluid volume from the markings;
   a processor communicatively coupled to the reader and configured to
   receive a first patient weight signal,
   use the at least one of the dialysis fluid type or the dialysis fluid volume from the markings in conjunction with the first patient weight signal to determine a first dialysis dwell time for a first dialysis dwell of a first cycle of a peritoneal dialysis therapy for a patient,
   begin a timer upon receiving an indication of a start of the first dialysis dwell,
   after the timer has reached the first dialysis dwell time, transmit a first output signal,
   receive a second patient weight signal,
   use the at least one of the dialysis fluid type or the dialysis fluid volume from the markings and the first dialysis dwell time in conjunction with the second patient weight signal to determine a second dialysis dwell time for a second dialysis dwell of a second cycle of the peritoneal dialysis therapy for the patient,
   begin the timer upon receiving an indication of a start of the second dialysis dwell, and
   after the timer has reached the second dialysis dwell time, transmit a second output signal; and
      an output interface configured to, in response to the first output signal, provide a first indication to the patient of a completion of the first dialysis dwell time, and in response to the second output signal, provide a second indication to the patient of a completion of the second dialysis dwell time,
   wherein the first and second indications each includes at least one of (i) a display of a visual notification on a screen of the output interface, (ii) an audio notification via a speaker of the output interface, or (iii) a tactile actuation via an actuator of the output interface.

2. The apparatus of claim 1, wherein the processor is configured to:
   determine an ultrafiltration trend based on the first and second patient weight signals; and
   cause the output interface to display the ultrafiltration trend.

3. The apparatus of claim 2, further comprising a transceiver configured to transmit the ultrafiltration trend and the at least one of the dialysis fluid type or the dialysis fluid volume to a remotely located computer to enable the computer to use the ultrafiltration trend and the at least one of the dialysis fluid type or the dialysis fluid volume to track a therapy progress of the patient.

4. The apparatus of claim 2, wherein the first and second patient weight signals each includes at least one of an actual patient weight or a weight of a dialysis fluid drain volume.

5. The apparatus of claim 1, wherein the first and second patient weight signals each includes at least one of an actual patient weight or a weight of a dialysis fluid drain volume.

6. The apparatus of claim 1, further comprising a start dwell input device communicatively coupled to the processor and configured to receive a first input from the patient corresponding to the indication of the start of the first dialysis dwell and receive a second input from the patient corresponding to the indication of the start of the second dialysis dwell.

7. The apparatus of claim 6, wherein the start dwell input device is provided by the output interface.

8. The apparatus of claim 1, wherein the reader includes (i) a barcode scanner, the markings displayed on the dialysis fluid containers comprising barcodes, (ii) a radio frequency identification ("RFID") reader, the markings displayed on the dialysis fluid containers comprising RFID tags, or (iii) a camera of a smartphone.

9. The apparatus of claim 1, wherein the handheld personal communication apparatus includes a smartphone.

10. The apparatus of claim 1, wherein the first and second dialysis dwell times each corresponds to a time to achieve at least one of (a) a specified ultrafiltration removal level for the cycle, (b) a urea removal level for the cycle, or (c) a creatinine removal level for the cycle.

11. A method for a continuous ambulatory peritoneal dialysis ("CAPD") treatment, the method comprising:
receiving, via a reader in a processor, at least one of a dialysis fluid type or a dialysis fluid volume from markings displayed on dialysis fluid containers;
receiving, in the processor, a first patient weight signal;
determining, via the processor, a first dialysis dwell time for a first dialysis dwell of a first cycle of a peritoneal dialysis therapy for a patient using the at least one of the dialysis fluid type or the dialysis fluid volume from the markings in conjunction with the first patient weight signal;
beginning, via the processor, a timer after receiving an indication of a start of the first dialysis dwell;
providing, via the processor and an output interface, a first indication to the patient of a completion of the first dialysis dwell time after the timer has reached the first dialysis dwell time;
receiving, in the processor, a second patient weight signal;
determining, via the processor, a second dialysis dwell time for a second dialysis dwell of a second cycle of the peritoneal dialysis therapy for the patient using the at least one of the dialysis fluid type or the dialysis fluid volume from the markings and the first dialysis dwell time in conjunction with the second patient weight signal;
beginning, via the processor, the timer after receiving an indication of a start of the second dialysis dwell; and
providing, via the processor and the output interface, a second indication to the patient of a completion of the second dialysis dwell time after the timer has reached the second dialysis dwell time,
wherein the first and second dialysis dwell times each corresponds to a time to achieve at least one of (a) a specified ultrafiltration removal level for the cycle, (b) a urea removal level for the cycle, or (c) a creatinine removal level for the cycle.

12. The method of claim 11, further comprising:
determining that each of the dialysis fluid containers has at least one of a different dialysis fluid volume or different dialysis fluid type;
providing, via the processor and the output interface, a first container indication regarding which of the dialysis fluid containers should be used for the first cycle; and
providing, via the processor and the output interface, a second container indication regarding which of the dialysis fluid containers should be used for the second cycle.

13. The method of claim 11, wherein the first and second indications each includes at least one of (i) a display of a visual notification on a screen of the output interface, (ii) an audio notification via a speaker of the output interface, or (iii) a tactile actuation via an actuator of the output interface.

14. The method of claim 11, further comprising:
determining, via the processor, an ultrafiltration trend based on the first and second patient weight signals; and
causing, via the processor, the output interface to display the ultrafiltration trend.

15. The method of claim 14, further comprising transmitting, via a transceiver, the ultrafiltration trend and the at least one of the dialysis fluid type or the dialysis fluid volume to a remotely located computer to enable the computer to use the ultrafiltration trend and the at least one of the dialysis fluid type or the dialysis fluid volume to track a therapy progress of the patient.

16. The method of claim 11, wherein the first and second patient weight signals each includes at least one of an actual patient weight or a weight of a dialysis fluid drain volume.

17. The method of claim 11, wherein the reader includes (i) a barcode scanner, the markings displayed on the dialysis fluid containers comprising barcodes, (ii) a radio frequency identification ("RFID") reader, the markings displayed on the dialysis fluid containers comprising RFID tags, or (iii) a camera of a smartphone.

18. The method of claim 11, wherein the reader, the processor, and the output interface are included within a smartphone.

* * * * *